US010835896B2

(12) United States Patent
Mi et al.

(10) Patent No.: US 10,835,896 B2
(45) Date of Patent: Nov. 17, 2020

(54) METHOD AND APPARATUS FOR CELL DISPENSING AND STORAGE

(71) Applicant: SCL BIOTECH LTD., Apia (WS)

(72) Inventors: Hsin-Wu Mi, New Taipei (TW); Ming-Cheng Lee, New Taipei (TW)

(73) Assignee: SCL BIOTECH LTD., Apia (WS)

(*) Notice: Subject to any disclaimer, the term of this patent is extended or adjusted under 35 U.S.C. 154(b) by 143 days.

(21) Appl. No.: 16/157,039

(22) Filed: Oct. 10, 2018

(65) Prior Publication Data

US 2020/0114344 A1 Apr. 16, 2020

(51) Int. Cl.

| B01L 3/00 | (2006.01) |
|---|---|
| B01L 1/00 | (2006.01) |
| B01L 1/02 | (2006.01) |
| B01L 9/06 | (2006.01) |
| B01L 7/00 | (2006.01) |
| B01L 9/00 | (2006.01) |

(52) U.S. Cl.
CPC ............... B01L 1/025 (2013.01); B01L 7/50 (2013.01); B01L 9/06 (2013.01); B01L 9/50 (2013.01); *B01L 2300/0609* (2013.01); *B01L 2300/1894* (2013.01)

(58) Field of Classification Search
CPC .. C12M 41/14; B01L 9/54; B01L 9/52; B01L 9/50; B01L 9/00; B01L 9/02
See application file for complete search history.

(56) References Cited

U.S. PATENT DOCUMENTS

| 6,673,595 B2* | 1/2004 | Barbera-Guillem ........................ C12M 23/24 435/286.2 |
|---|---|---|
| 9,279,099 B2* | 3/2016 | Okano .................... C12M 23/44 |
| 2006/0257999 A1* | 11/2006 | Chang ..................... C40B 60/06 435/289.1 |
| 2006/0275888 A1* | 12/2006 | Hibino ................... C12M 41/14 435/286.2 |
| 2009/0246081 A1* | 10/2009 | Nichols .................. G01N 35/04 422/63 |
| 2010/0294046 A1* | 11/2010 | Boeke ..................... C12M 33/07 73/863.01 |
| 2011/0042582 A1* | 2/2011 | Ingber ................. G01N 21/0332 250/458.1 |
| 2013/0203072 A1* | 8/2013 | Tian .......................... G01N 1/31 435/7.1 |
| 2016/0002584 A1* | 1/2016 | Nozaki ................... C12M 23/50 435/289.1 |

(Continued)

*Primary Examiner* — Nathan A Bowers
(74) *Attorney, Agent, or Firm* — Pai Patent & Trademark Law Firm; Chao-Chang David Pai

(57) ABSTRACT

Provided are a cell dispensing and storing apparatus and a method of the same. The method includes: moving a freezing container with a test tube in it and a temporary storage bottle containing sample cells into a dispensing area. Connect the temporary storage bottle with an injecting assembly. A dispensing clamp moves the test tube from the freezing container to a tube rack on a rotating platform. A rotating clamp removes a tube cover from the test tube. An injecting nozzle extracts the sample cells from the temporary storage bottle and dispenses the sample cells into the test tube. The rotating clamp puts the tube cover back on the test tube. The dispensing clamp moves the test tube back into the freezing container. A freezing clamp moves the freezing container into a freezer.

6 Claims, 14 Drawing Sheets

(56) References Cited

U.S. PATENT DOCUMENTS

2017/0137770 A1\* 5/2017 Sakamoto ............. C12M 29/14
2019/0119621 A1\* 4/2019 Koike ................... G06T 7/0012

\* cited by examiner

METHOD AND APPARATUS FOR CELL DISPENSING AND STORAGE

BACKGROUND OF THE INVENTION

1. Field of the Invention

The present invention relates to a method and an apparatus for cell dispensing and storage, especially to an automated method and an automated apparatus for cell dispensing and storage.

2. Description of the Prior Arts

During the collection, processing, and storage of sample cells, if the sample cells are exposed to germs or other contaminations, the sample cells can be easily infected and lose the characteristics that are targeted for inspection. Therefore, when processing sample cells, a user must operate in a sterile room or in a place that is environmentally safe for such sample cells.

In a conventional way of storing sample cells, the user first dispenses the sample cells from a temporary storage bottle into multiple test tubes (cyrotube), covers the test tubes and then stores the sample-cell-containing test tubes into a liquid nitrogen tank.

However, because the conventional dispensing and storing method for sample cells is manually operated, it is highly likely for the sample cells to lose the characteristic for inspection due to accidental infection by germs or other contaminations from the exterior environment, for example, during a process when the sample cells are about to be moved out of the temporary storage bottle and dispensed into the test tubes. Therefore, the conventional dispensing and storing method for sample cells is defective.

To overcome the shortcomings, the present invention provides a method and apparatus for cell dispensing and storage to mitigate or obviate the aforementioned problems.

SUMMARY OF THE INVENTION

The main objective of the present invention is to provide a method and apparatus for cell dispensing and storage that lowers the risk of sample cells infection and also making the dispensing and storing process less labor-intensive by automating the dispensing and storing process.

The cell dispensing and storing apparatus has a feeding area, a transferring area, a dispensing area, and a freezing area. The feeding area comprises a feeding opening formed on a wall of the feeding area and communicating with an exterior environment.

The transferring area selectively communicates with the feeding area and comprises a transferring clamp and at least one operating opening. The transferring clamp is movably disposed in the transferring area. The at least one operating opening is formed on a wall of the transferring area.

The dispensing area selectively communicates with the transferring area and comprises a dispensing platform, a dispensing base, a rotating cylinder, at least one rotating clamp, a rotating platform, multiple tube racks, a dispensing clamp, and an injecting assembly. The dispensing platform is mounted in the dispensing area. The dispensing base is movably mounted on the dispensing platform and is capable of moving from the dispensing area into the transferring area. The rotating cylinder is rotatably mounted on the dispensing platform. The at least one rotating clamp is mounted on the rotating cylinder and is capable of moving up and down relative to the rotating cylinder. The rotating platform is rotatably mounted on the dispensing platform and is capable of rotating relative to the rotating cylinder. The tube racks are mounted on the rotating platform and surround the rotating cylinder. Also, the tube racks are capable of rotating relative to the rotating cylinder through a rotation of the rotating platform. The at least one rotating clamp is capable of moving to a top of each one of the tube racks. The dispensing clamp is mounted on the dispensing platform and is capable of moving to a top of the dispensing base and to the top of one of the tube racks. The injecting assembly is mounted on the dispensing platform and comprises a nozzle rack, an injecting nozzle, and an injecting pipe. The nozzle rack is mounted on the dispensing platform. The injecting nozzle is mounted on the nozzle rack and is disposed on the top of one of the tube racks. One end of the injecting pipe is connected to the injecting nozzle.

The freezing area selectively communicates with the transferring area and comprises a freezer and a freezing clamp. The freezer is mounted in the freezing area. The freezing clamp is movably mounted in the freezing area and is capable of moving into the freezer. The freezing clamp selectively corresponds in position to the freezer.

The cell dispensing and storing method has steps of:
step (a) preparing a temporary storage bottle, a freezing container, a container cover, a transferring area, a transferring clamp, a dispensing area, and a freezing area, wherein sample cells are contained in the temporary storage bottle; a test tube is disposed in the freezing container; the container cover covers the freezing container; the transferring clamp is disposed in the transferring area; the dispensing area comprises a dispensing base, a dispensing clamp, a rotating cylinder, a rotating platform, a tube rack and an injecting assembly; a rotating clamp is mounted on the rotating cylinder; the injecting assembly comprises a nozzle rack, an injecting nozzle, and an injecting pipe; the freezing area comprises a freezer and a freezing clamp;

step (b) transferring the test tube, wherein the dispensing base is moved from the dispensing area into the transferring area; the freezing container is put on the dispensing base, and the transferring clamp removes the container cover from the freezing container; the dispensing base moves the freezing container from the transferring area back into the dispensing area, then the dispensing clamp transfers the test tube in the freezing container into the tube rack on the rotating platform; the nozzle rack is mounted in the dispensing area, the injecting nozzle is mounted on the nozzle rack, the temporary storage bottle and the injecting pipe are both disposed in the injecting assembly, and two ends of the injecting pipe are respectively connected to the injecting nozzle and the temporary storage bottle;

step (c) opening the test tube, wherein the rotating platform moves the tube rack through a rotation of the rotating platform and moves the tube rack to a position below the rotating clamp of the rotating cylinder, then the rotating clamp moves downwardly, removes a tube cover of the test tube from the test tube and then moves back upwardly with the tube cover;

step (d) injecting the sample cells, wherein the tube rack is moved by the rotating platform to a site adjacent to the injecting assembly, and then the injecting nozzle extracts the sample cells from the temporary storage bottle and injects the sample cells into the test tube;

step (e) closing the test tube, wherein the rotating cylinder and the rotating platform respectively move the rotating clamp and the test tube to make the test tube disposed below the rotating clamp, and then the rotating clamp moves downwardly and covers the tube cover back onto the test tube; step (f) transferring the freezing container, wherein the rotating platform moves the tube rack to a site adjacent to the dispensing clamp, and the dispensing clamp transfers the test tube from the tube rack into the freezing container;

step (g) storing the freezing container, wherein the dispensing base moves the freezing container from the dispensing area into the transferring area, the transferring clamp covers the container cover back onto the freezing container, then the transferring clamp transfers the freezing container from the transferring area into the freezing area, and the freezing clamp transfers the test tube into the freezer.

Given the foregoing steps of the method and structure of the apparatus for cell dispensing and storage, the present invention is capable of fully automatizing the dispensing and storing process for sample cells. Specifically, the freezing container, which contains multiple test tubes, is first put into the feeding area through the feeding opening. Then the freezing container is moved to the transferring area. Meanwhile, the dispensing base moves to the transferring area from the dispensing area. When the freezing container is moved to the transferring area, the transferring clamp removes the container cover from the freezing container, and then the freezing container is transferred to the dispensing base. Then the dispensing base moves the freezing container and the test tube from the transferring area back to the dispensing area. After the freezing container is moved into the dispensing area, the dispensing clamp moves the test tube from the freezing container to the corresponding tube rack. After that, the rotating clamp from the rotating cylinder removes the tube cover from the test tube. By the rotation of the tube rack, the test tube will pass through a position below the injecting assembly, and the injecting nozzle will inject sample cells from the temporary storage bottle to the test tube. After the injection, the test tube will be moved away from the injecting assembly by the rotation of the tube rack, and the rotating clamp of the rotation cylinder puts the tube cover back to the test tube. The dispensing clamp transfers the covered test tube back to the freezing container, and the dispensing base moves the freezing container back to the transferring area from the dispensing area. After the transferring clamp puts the container cover back onto the freezing container, the transferring clamp moves the covered freezing container to the freezing area and finishes the whole dispensing and storing process.

By the automatizing process, the present invention enhances the germ-prevention in the dispensing area, therefore lowers the risk of the sample cells infection, and also lowers the labor intensiveness for the dispensing process.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
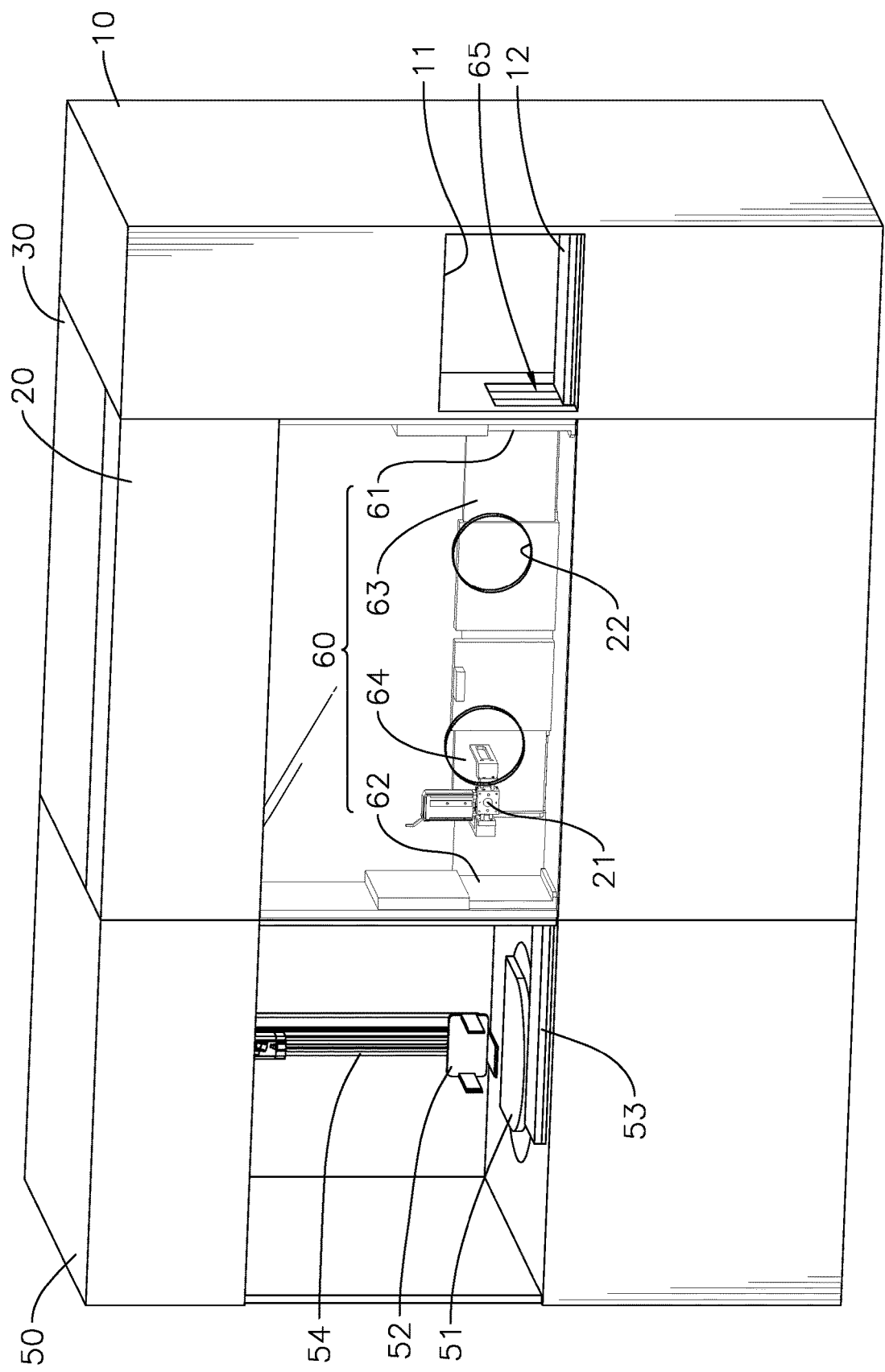
FIG. 1 is a perspective view of a cell dispensing and storing apparatus in accordance with the present invention.
Figure 4:
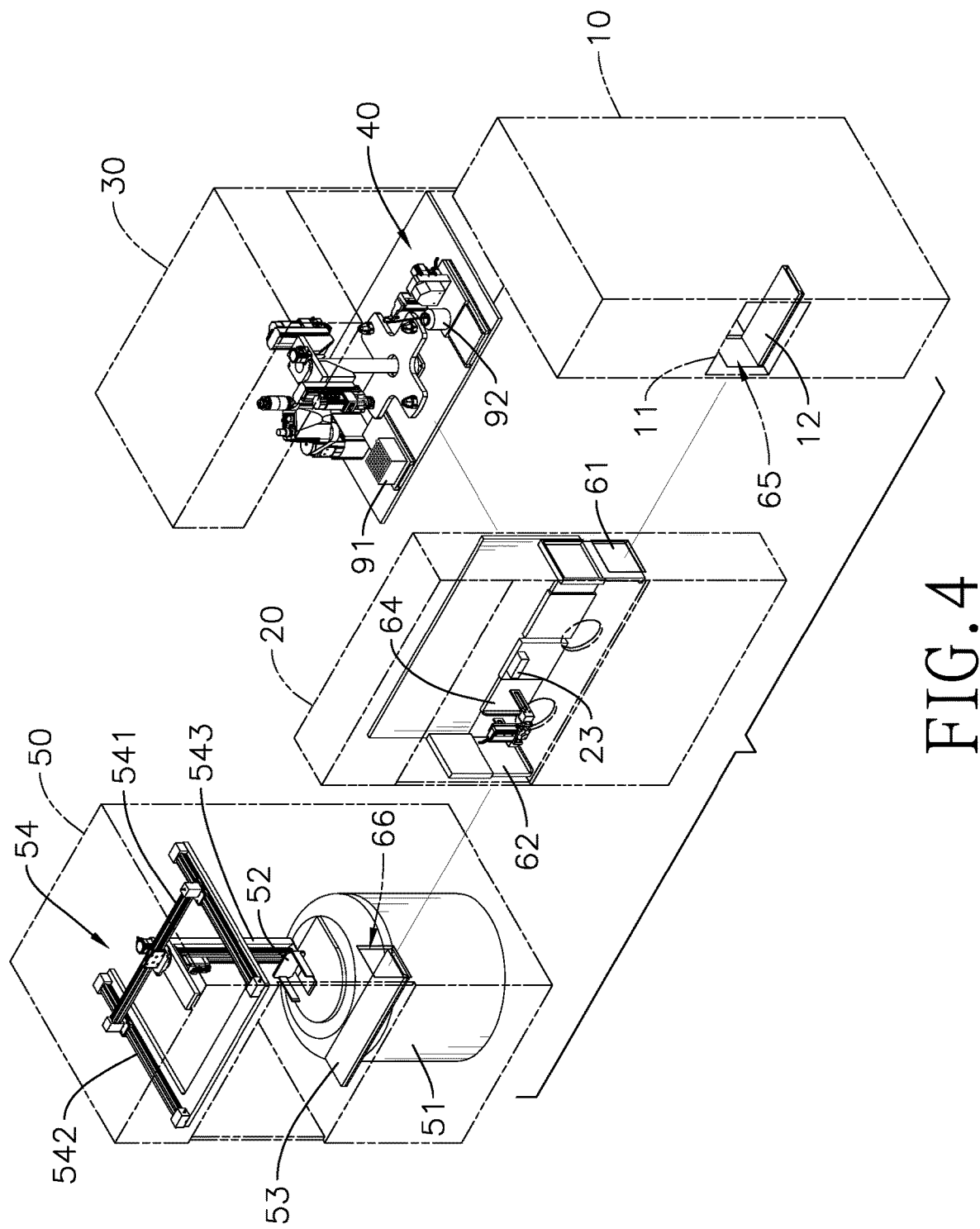
FIGS. 4 and 5 are exploded perspective views of the cell dispensing and storing apparatus in FIG. 1.

With reference to FIGS. 1 and 4, a cell dispensing and storing apparatus in accordance with the present invention comprises a feeding area 10, a transferring area 20, a dispensing area 30, an injecting assembly 40, a freezing area 50, and a gate assembly 60.

Figure 3:
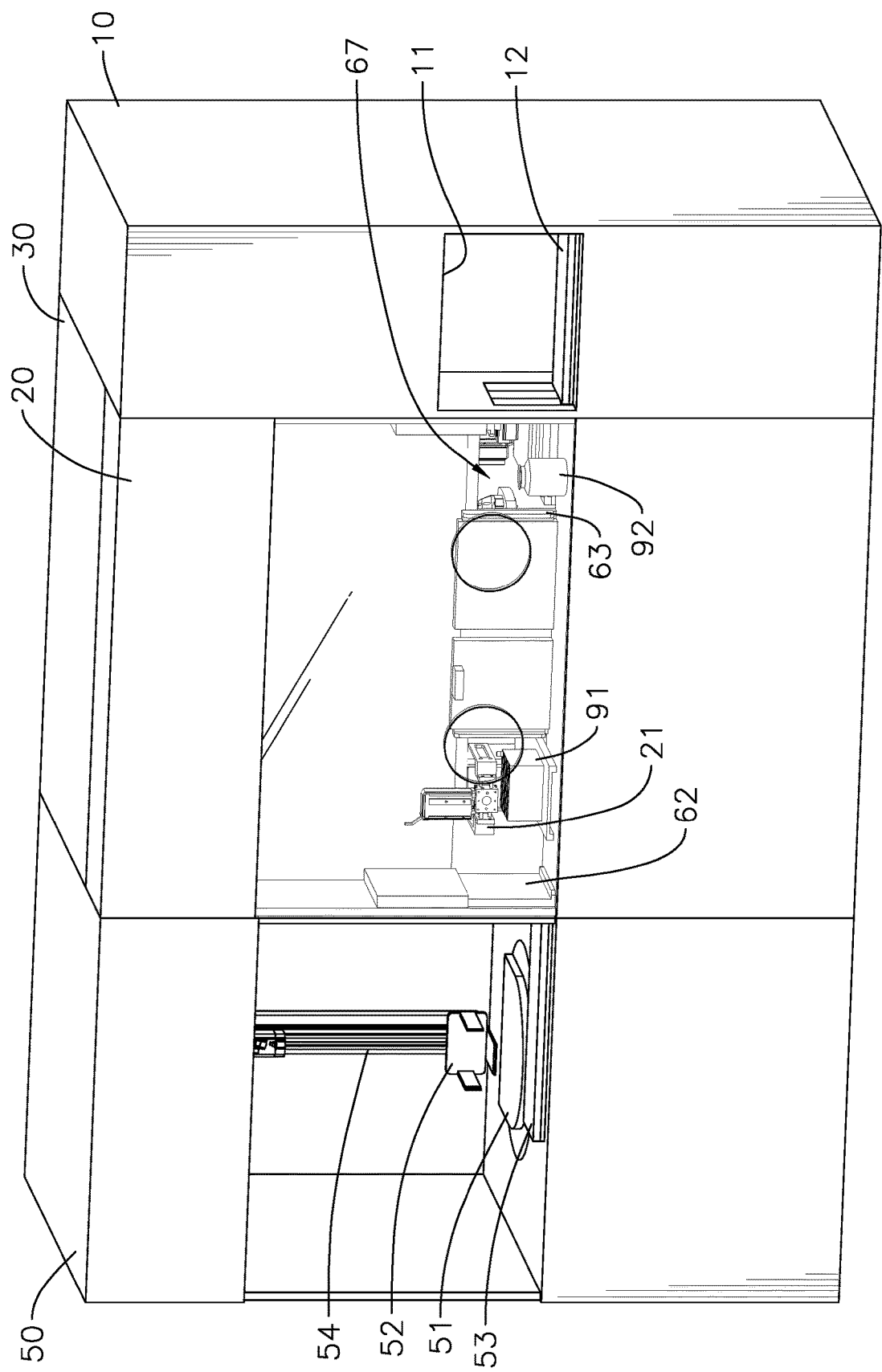
FIG. 3 is a perspective view of a freezing container and a temporary storage bottle being transferred to the transferring area of the cell dispensing and storing apparatus in FIG. 1.
Figure 5:
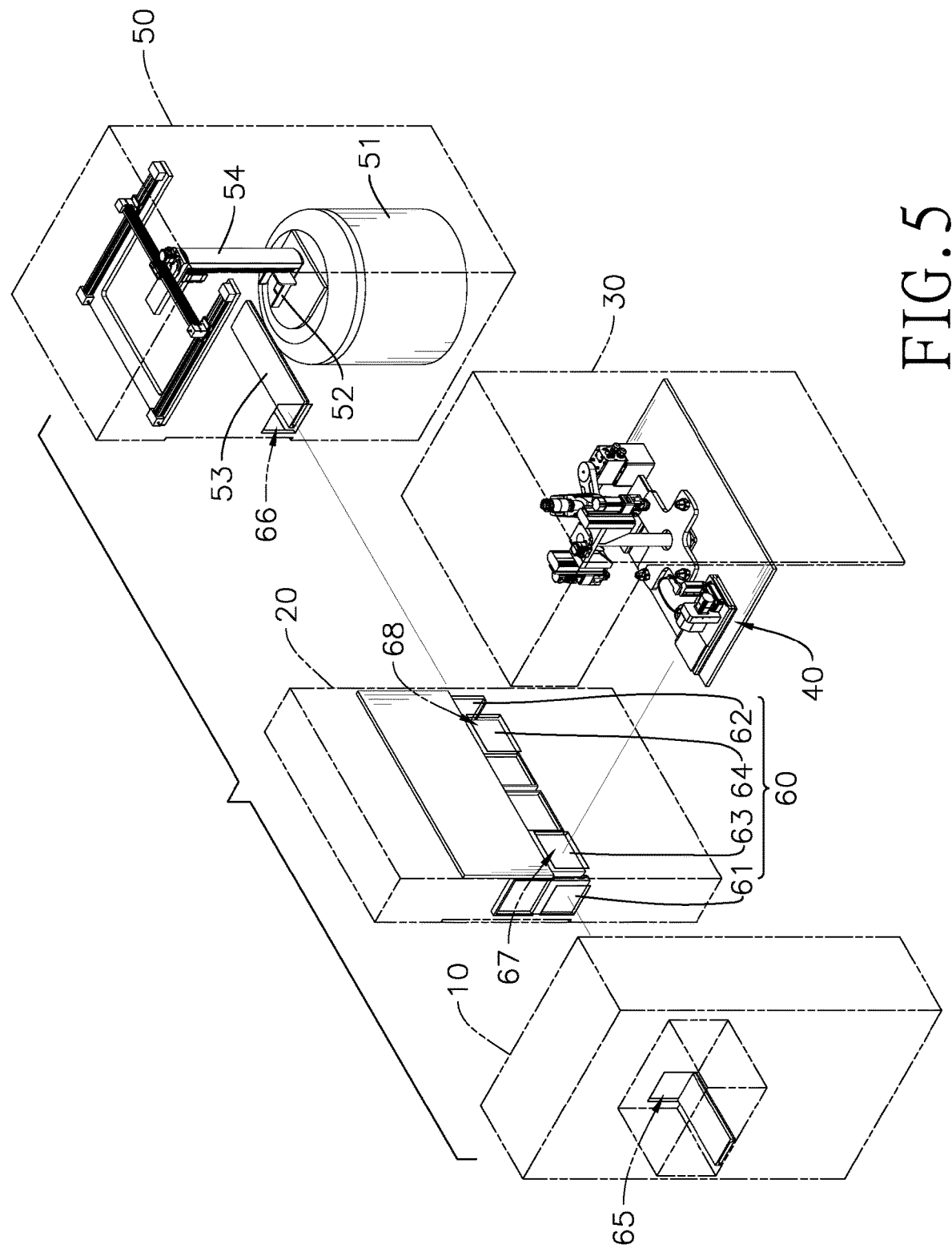

With reference to FIGS. 3, 4, and 5, in the present embodiment, the transferring area 20 is a rectangular box. Four side surfaces of the transferring area 20 are respectively facing the feeding area 10, the dispensing area 30, the freezing area 50, and an exterior environment. Furthermore, in the present embodiment, the selectively communicating relations between the transferring area 20 and the feeding area 10, between the transferring area 20 and the dispensing area 30, and between the transferring area 20 and the freezing area 50 are controlled by the gate assembly 60.

With reference to FIGS. 4 and 5, specifically, the gate assembly 60 comprises an entrance gate 61, an exit gate 62, a transferring gate 63, and a container gate 64. The entrance gate 61 is mounted between the feeding area 10 and the transferring area 20, and the entrance gate 61 selectively closes up a first opening 65 between the feeding area 10 and the transferring area 20. The exit gate 62 is mounted between the transferring area 20 and the freezing area 50, and the exit gate 62 selectively closes up a second opening 66 between the transferring area 20 and the freezing area 50. The transferring gate 63 and the container gate 64 are mounted between the transferring area 20 and the dispensing area 30, and are arranged apart from each other. The transferring gate 63 and the container gate 64 respectively and selectively close up a third opening 67 and a fourth opening 68, which are both formed between the transferring area 20 and the dispensing area 30. Meanwhile, the transferring gate 63 is adjacent to the feeding area 10, and the container gate 64 is adjacent to the freezing area 50.

When the gates 61, 62, 63, and 64 of the gate assembly 60 are all closed, the transferring area 20, the dispensing area 30, and the freezing area 50 each form an enclosed space, but in other embodiments, the enclosed space for each area 20, 30, and 50 is optional; in other words, even without the gate assembly 60, the present invention can also achieve the purpose of "automatic dispensing", but with the enclosing function from the gate assembly 60, the present invention may further lower the risk of sample cell infection during the dispensing process.

The present invention achieves the purpose of selectively closing up the communication between areas by the gate assembly 60, but it is not limited thereto, as a user may reach this purpose by other means.

Figure 2:
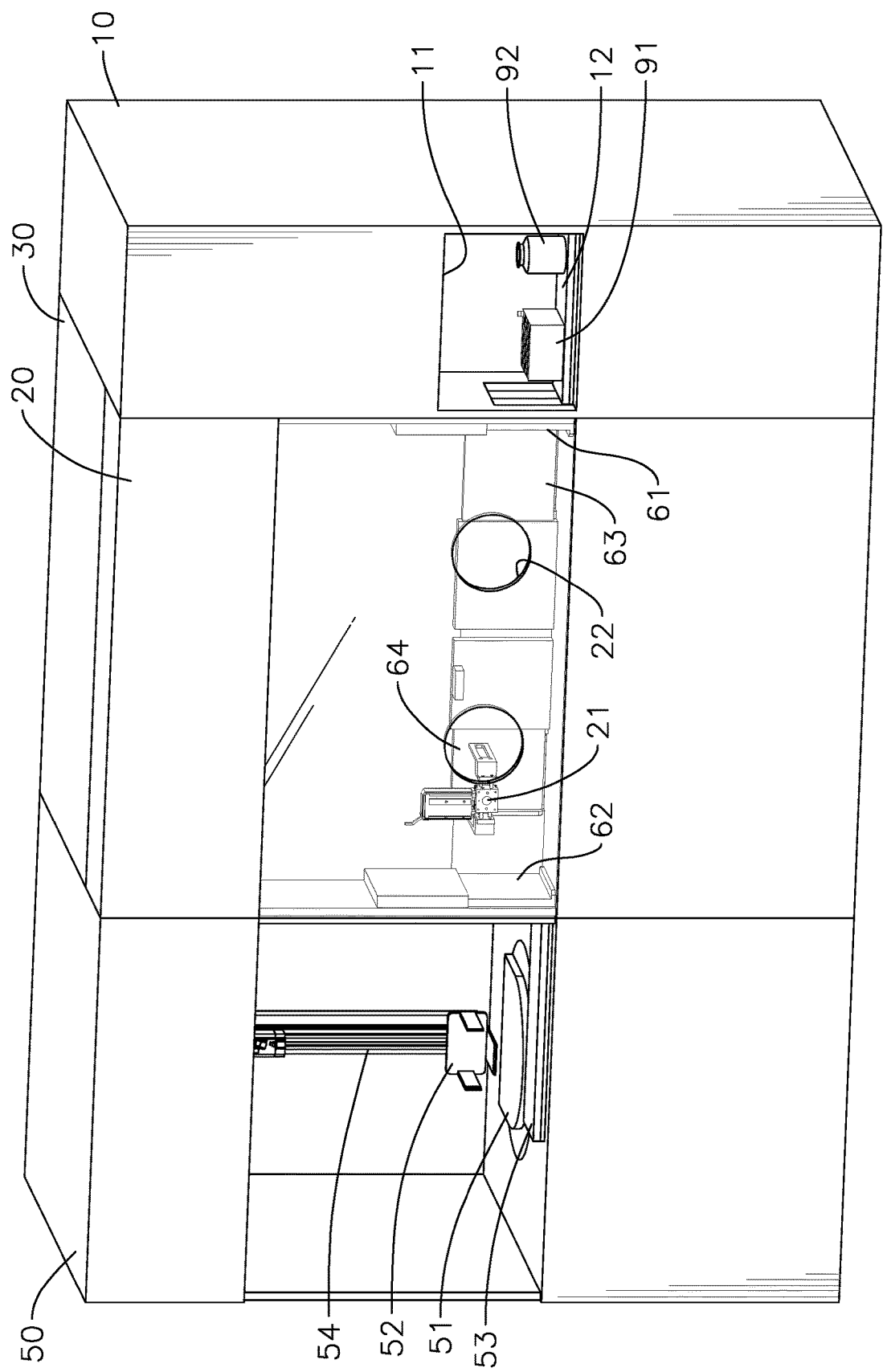
FIG. 2 is a perspective view of the cell dispensing and storing apparatus in FIG. 1 with a freezing container and a temporary storage bottle.

With reference to FIGS. 1, 2, and 5, the feeding area 10 comprises a feeding opening 11 and a feeding cart 12. The feeding opening 11 is formed on a wall of the feeding area 10 and communicates with the exterior environment. The user may put an object into the feeding area 10 through the feeding opening 11. The feeding cart 12 is disposed in the feeding area 10, and can move from the feeding area 10 into the transferring area 20. Specifically, in the present embodiment, the feeding cart 12 can move back and forth between the feeding area 10 and the transferring area 20 through the first opening 65, but it is not limited thereto. Besides, in another embodiment, the feeding area 10 can be a biosafety cabinet.

With reference to FIGS. 1 to 4, the transferring area 20 comprises a transferring clamp 21, at least one operating opening 22, and a freezing container scanner 23. The transferring clamp 21 is movably disposed in the transferring area 20. Specifically, in the present embodiment, the transferring clamp 21 is capable of moving in a three-dimensional space in the transferring area 20 by moving on a track assembly (not shown in the figures) that is mounted in the transferring area 20.

The at least one operating opening 22 is mounted on the side surface of the transferring area 20 that faces the exterior environment. In the present embodiment, a number of the at least one operating opening 22 is two, and the two operating openings 22 correspond in position respectively to the transferring gate 63 and the container gate 64. The freezing container scanner 23 is mounted in the transferring area 20 and is adjacent to the two operating openings 22.

In the present embodiment, two gloves (not shown in figures) are each respectively mounted on and surround the two operating openings 22. Each glove is mounted around an edge of the corresponding operating opening 22 and extends into the transferring area 20. In other words, the user may put hands in the gloves to stretch hands into the transferring area 20 without directly contacting the interior of the transferring area 20. That is, the gloves prevent the transferring area 20 from communicating with the exterior environment through the two operating openings 22.

When the user stretches hands into the transferring area 20 through the glove and the operating openings 22, the user can pick up a freezing container 91 and move it to the freezing container scanner 23, which is near the operating openings 22, for scanning, and therefore the freezing container scanner 23 may record data from said freezing container 91.

Figure 6:
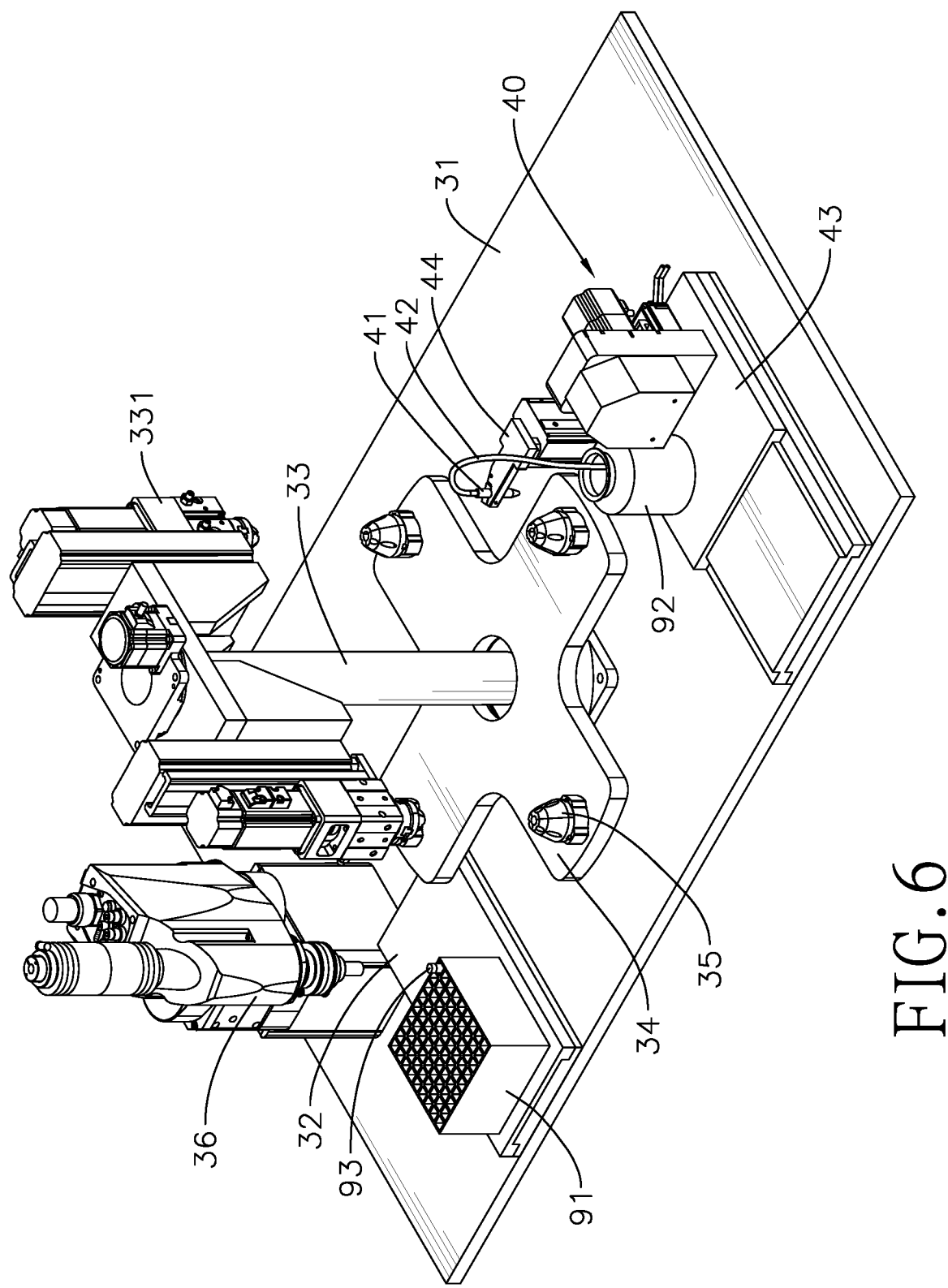
FIGS. 6 to 13 are the operational views of sample cells being dispensed to a test tube by the cell dispensing and storing apparatus in FIG. 1.
Figure 7:
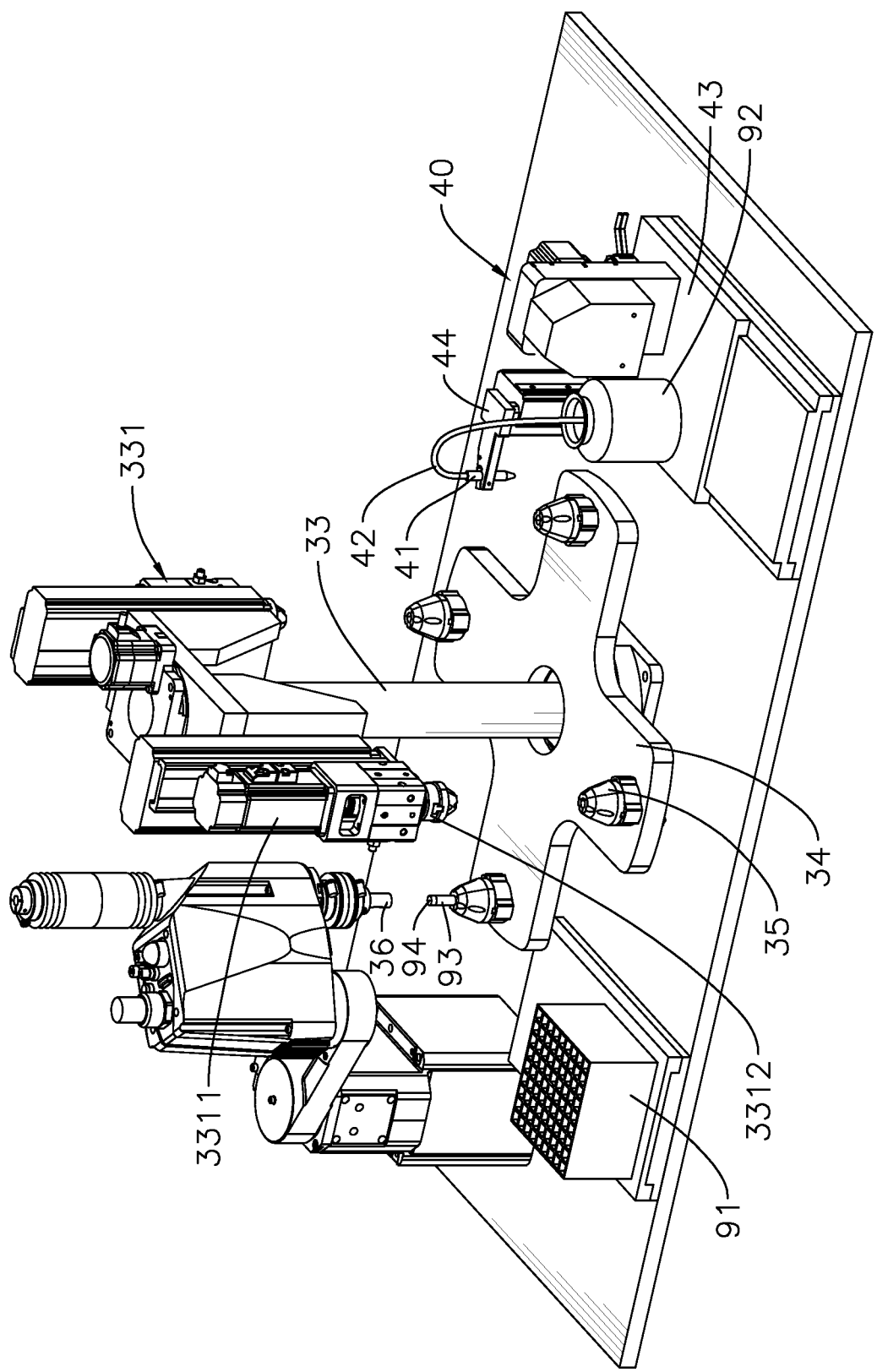

With reference to FIGS. 5, 6, and 7, the dispensing area 30 comprises a dispensing platform 31, a dispensing base 32, a rotating cylinder 33, a rotating platform 34, multiple tube racks 35, and a dispensing clamp 36.

The dispensing base 32 is movably mounted on the dispensing platform 31, and corresponds in position to the container gate 64. Specifically, when the container gate 64 is open, the dispensing base 32 is capable of moving from the dispensing area 30 into the transferring area 20 through the fourth opening 68, and the transferring clamp 21 is capable of moving to a top of the dispensing base 32 when the dispensing area 30 is in the transferring area 20.

The rotating cylinder 33 is rotatably mounted on the dispensing platform 31, and comprises at least one rotating clamp 331 mounted thereon. In the present embodiment, a number of the at least one rotating clamp 331 is, but not limited to, two, and each one of the two rotating clamps 331 is capable of moving up and down relative to the rotating cylinder 33. The two rotating clamps 331 are arranged apart from each other on the rotating cylinder 33 and surround the rotating cylinder 33.

Specifically, in the present embodiment, each rotating clamp 331 horizontally extends from the rotating cylinder 33, but the relative position between each rotating clamp 331 and the rotating cylinder 33 is not limited thereto.

Figure 8:
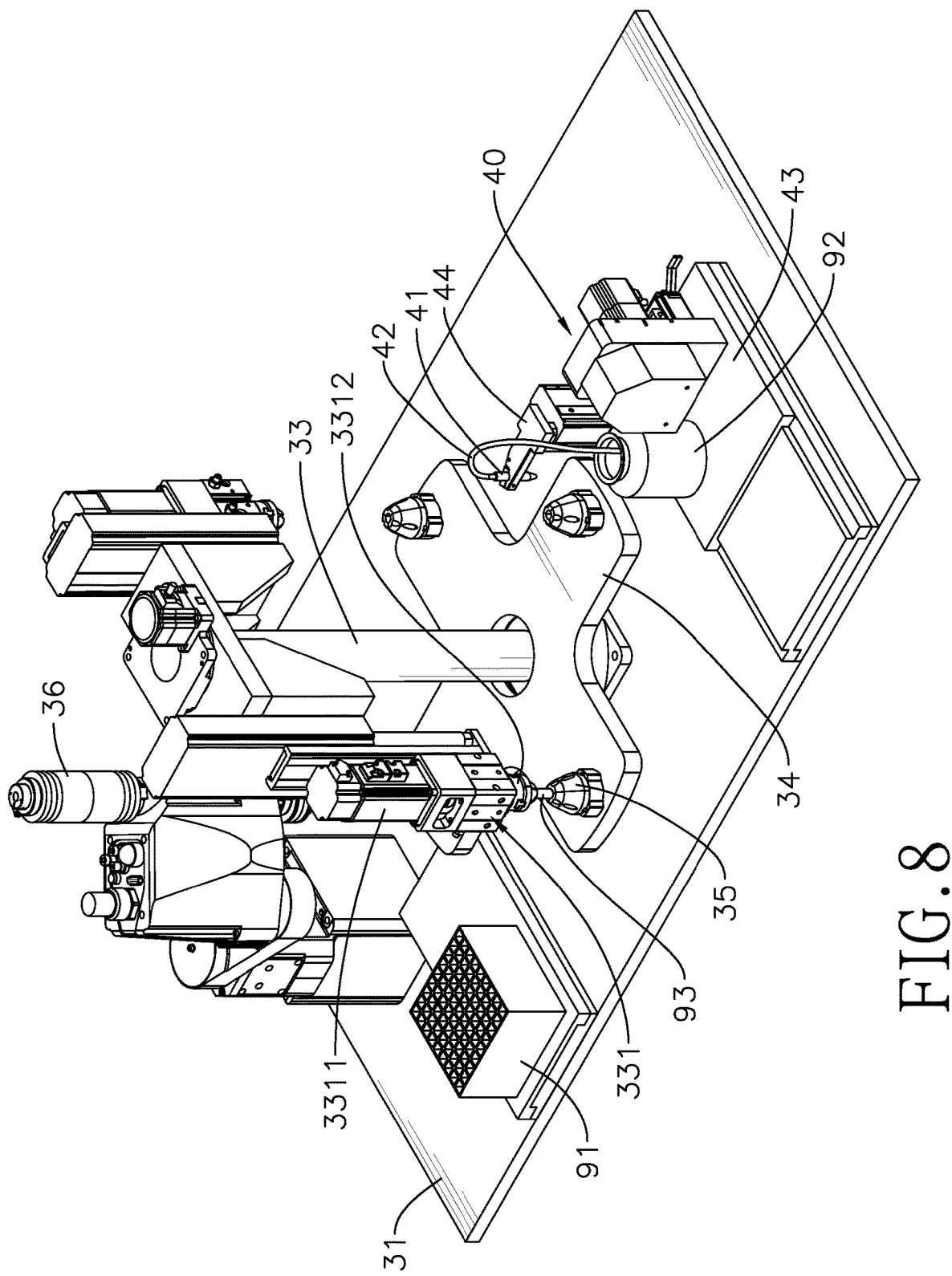
Figure 9:
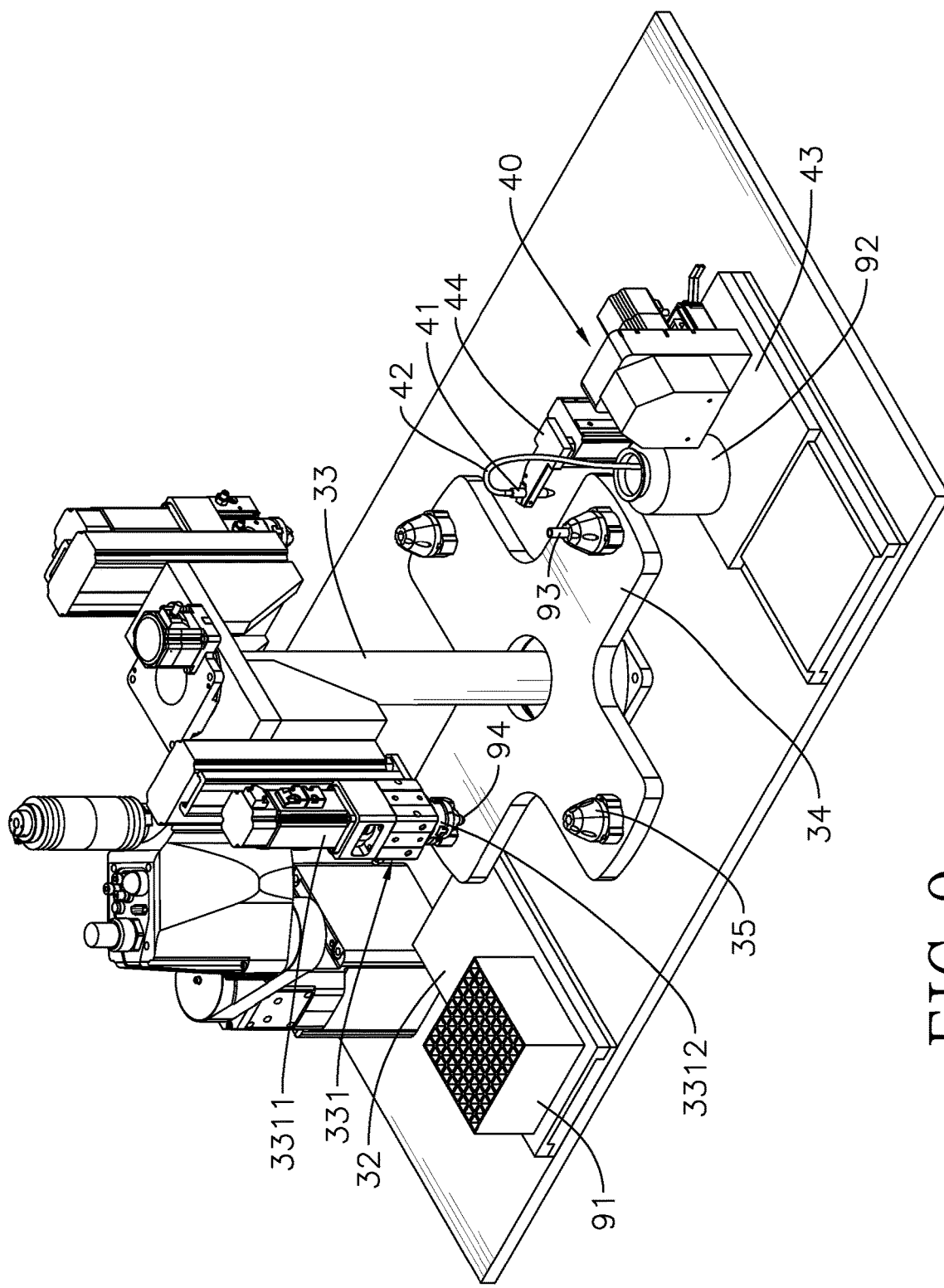

Besides, with reference to FIGS. 7, 8, and 9, in the present embodiment, each rotating clamp 331 is capable of self-rotating. Specifically, the rotating clamp 331 has a mounting segment 3311 and a clamping segment 3312. The mounting segment 3311 is mounted on the rotating cylinder 33 and is capable of moving up and down relative to the rotating cylinder 33. The clamping segment 3312 is mounted on the mounting segment 3311 and is capable of rotating relative to the mounting segment 3311. The purpose of self-rotating is as follows: because the rotating clamp 331 is used to remove a tube cover 94 of a test tube 93 from said test tube 93, the clamping segment 3312 which is capable of rotating relative to the mounting segment 3311 is suitable for the tube cover 94 that is mounted on a test tube 93 by screwing. However, in other embodiments, when the tube cover 94 is mounted on the test tube 93 by engagement, the rotating clamp 331 may be designed to move up and down relative to the rotating cylinder 33 to remove or mount the tube cover 94 on the test tube 93.

The rotating platform 34 is mounted on the dispensing platform 31, and is rotatable relative to the rotating cylinder 33. Specifically, in the present embodiment, the rotating cylinder 33 is mounted through a center of the rotating platform 34 and extends downwardly to be rotatably connected to the dispensing platform 31, but the relative position between the rotating cylinder 33 and the rotating platform 34 is not limited thereto.

The tube racks 35 are mounted on the rotating platform 34, which surrounds the rotating cylinder 33, and rotation of the rotating platform 34 moves the tube racks 35 relative to the rotating cylinder 33. Specifically, the tube racks 35 are capable of moving around the rotating cylinder 33 by the rotation of the rotating platform 34. The two rotating clamps 331 are capable of moving to a top of each tube rack 35.

The dispensing clamp 36 is mounted on the dispensing platform 31, and is capable of moving to the top of one of the tube racks 35 on the dispensing base 32. Specifically, in the present embodiment, the dispensing clamp 36 is pivotally mounted on the dispensing platform 31. By pivoting relative to the dispensing platform 31, the dispensing clamp 36 is capable of moving from the dispensing base 32 to the top of the tube rack 35 that is the closest to the dispensing clamp 36. However, a means of movement of the dispensing clamp 36 (for example, by pivoting in the present embodiment) is not limited thereto.

Figure 10:
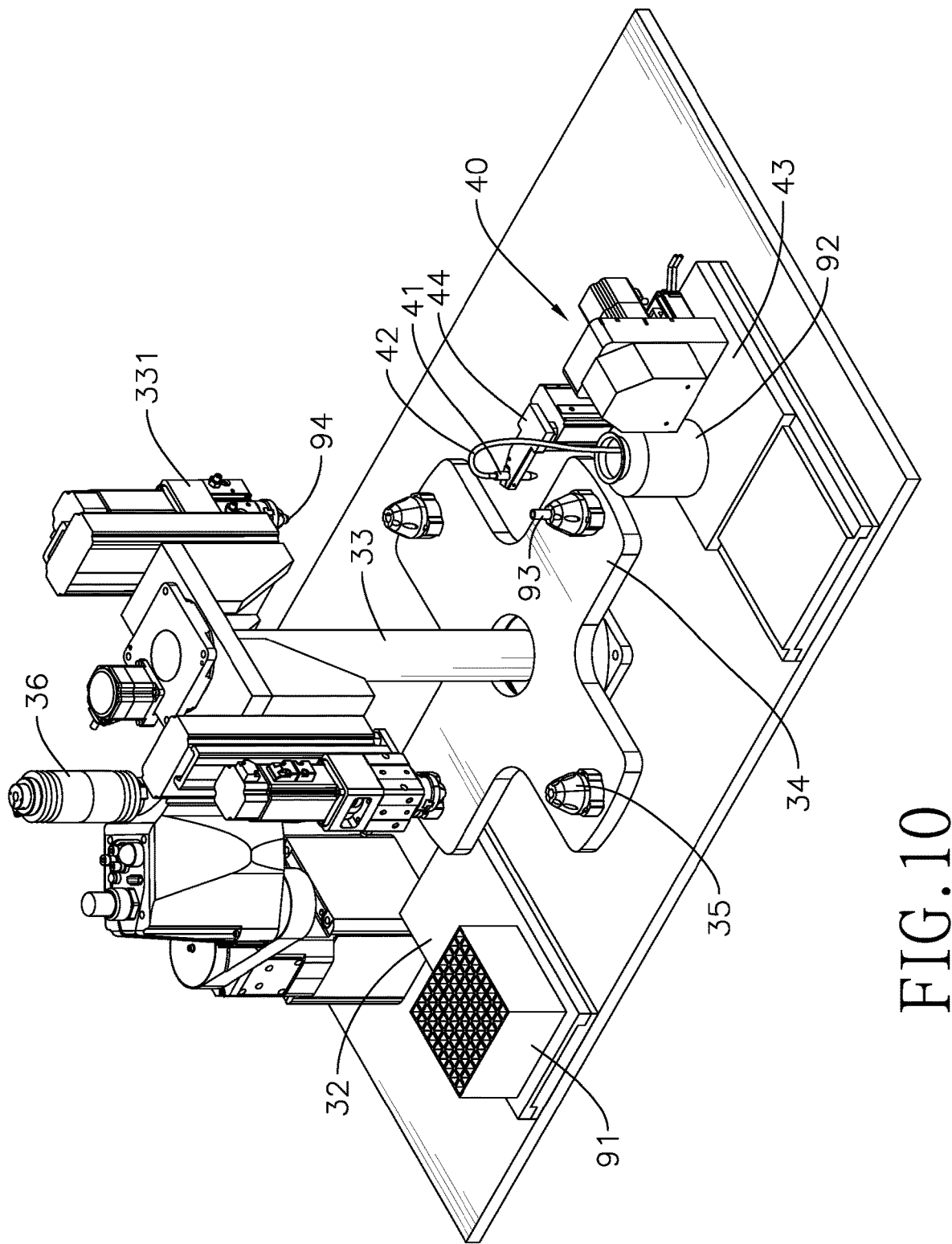
Figure 11:
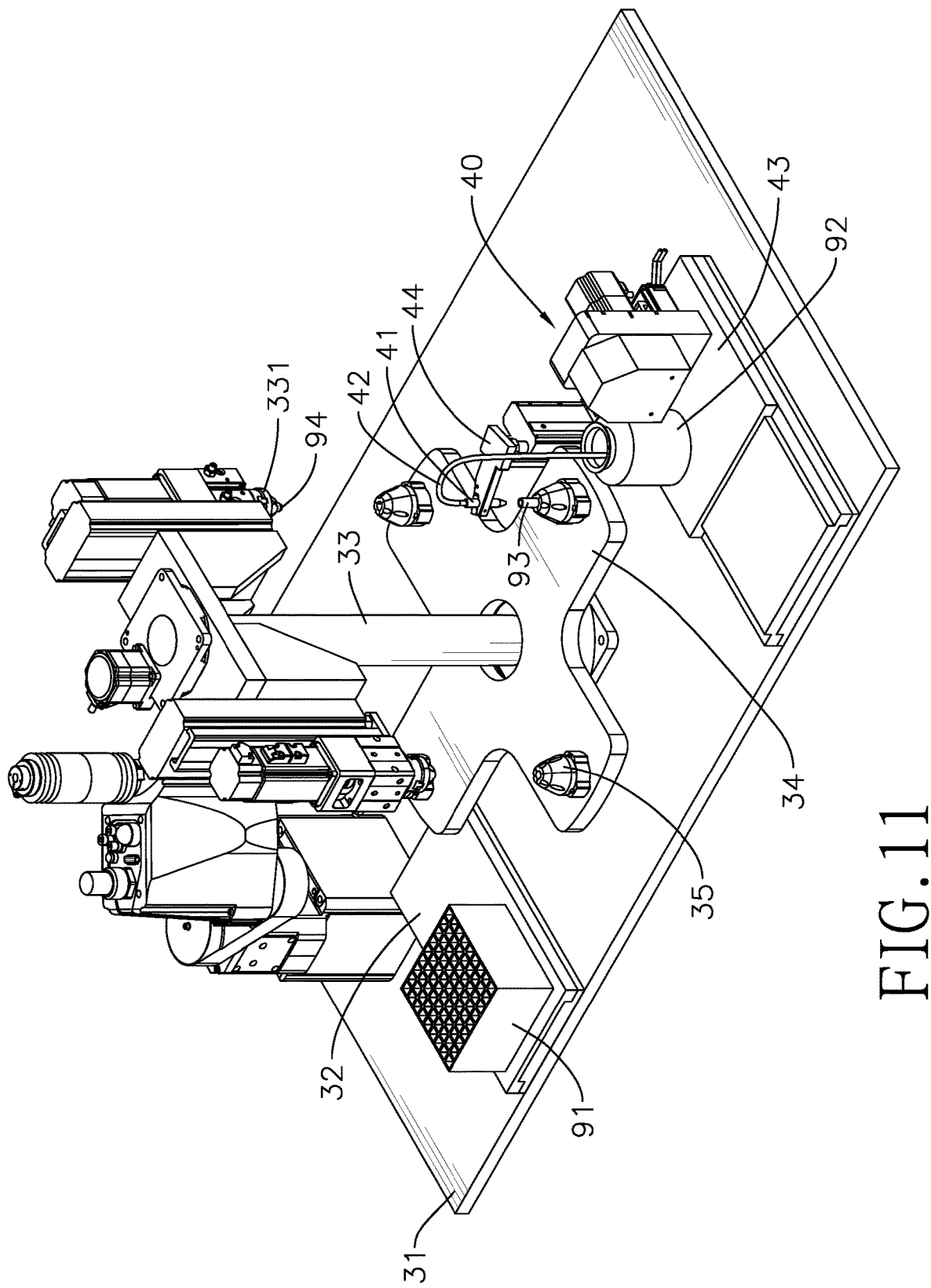

With reference to FIGS. 10 and 11, the injecting assembly 40 is mounted on the dispensing platform 31 and comprises an injecting nozzle 41, an injecting pipe 42, a nozzle base 43, and a nozzle rack 44.

The nozzle base 43 is mounted on the dispensing platform 31, and is capable of moving relative to the dispensing platform 31. The nozzle rack 44 is mounted on the nozzle base 43. The injecting nozzle 41 is mounted on the nozzle rack 44 and is disposed on top of one of the tube racks 35. Specifically, in the present embodiment, the nozzle rack 44 is capable of rotating relative to the nozzle base 43, so the injecting nozzle 41 can selectively move to the top of one of the tube racks 35. Alternatively, each tube rack 35 directly moves to a position below the injecting nozzle through the rotation of the rotating platform 34.

An end of the injecting pipe 42 is connected to the injecting nozzle 41. In the present embodiment, the injecting assembly 40 extracts sample cells from the temporary storage bottle 92 to the injecting nozzle 41 through a peristaltic pump, but the extracting method and means are not limited thereto.

Furthermore, the position of the transferring gate 63 corresponds to a position of the injecting assembly 40, and the nozzle base 43 is capable of moving from the dispensing area 30 into the transferring area 20 through the third opening 67.

With reference to FIG. 6, in the present embodiment, the configurations of the elements disposed inside the dispensing area 30 are as follows: the rotating cylinder 33 is mounted between the transferring gate 63 and the container gate 64. The dispensing base 32 and the injecting assembly 40 are respectively mounted on two opposite sides of the rotating cylinder 33. The dispensing base 32 is adjacent to the container gate 64. The injecting assembly 40 is adjacent to the transferring gate 63. The dispensing clamp 36 is adjacent to the dispensing base 32. In other words, when a tube rack 35 moves around the rotating cylinder 33 from a site adjacent to the dispensing base 32 to a site adjacent to the injecting assembly 40, a rotation angle of said tube rack 35 relative to the rotating cylinder 33 is 180 degrees. In a preferred embodiment, the configurations of the elements in the dispensing area 30 are as shown above, but it is not limited thereto.

With reference to FIGS. 1 and 4, the freezing area 50 comprises a freezer 51, a freezing clamp 52, a freezing cart 53, and a freezer cover 55. The freezing clamp 52 is movably mounted in the freezing area 50, and is capable of moving into the freezer 51. In other words, a position of the freezing clamp 52 and a position of the freezer 51 are selectively corresponding to each other.

In the present embodiment, the freezing clamp 52 is capable of moving in the freezing area 50 and into the freezer 51 by moving on a track assembly 54 that is mounted inside the freezing area 50, specifically, the track assembly 54 comprises a first track 541, a second track 542, and a third track 543, the tracks 541, 542, 543 respectively represent the x-axis, the y-axis, and the z-axis of the freezing clamp 52, so the freezing clamp 52 is capable of moving in a three-dimensional space in the freezing area 50 by the track assembly 54, but the means of moving of the freezing clamp 52 is not limited thereto. Besides, in the present embodiment, the transferring clamp 21 has a same moving structure as the freezing clamp 52 (the track assembly), but it is also not limited thereto.

With reference to FIGS. 4 and 5, in the present embodiment, the freezing cart 53 can move back and forth between the freezing area 50 and the transferring area 20 through the second opening 66 when the exit gate 62 is not closed. Furthermore, when the freezing cart 53 moves into the transferring area 20, a freezing container 91 can be put on the freezing cart 53 by the transferring clamp 21 from the transferring area 20, so the freezing cart 53 may move the freezing container 91 into the freezing area 50.

Figure 14:
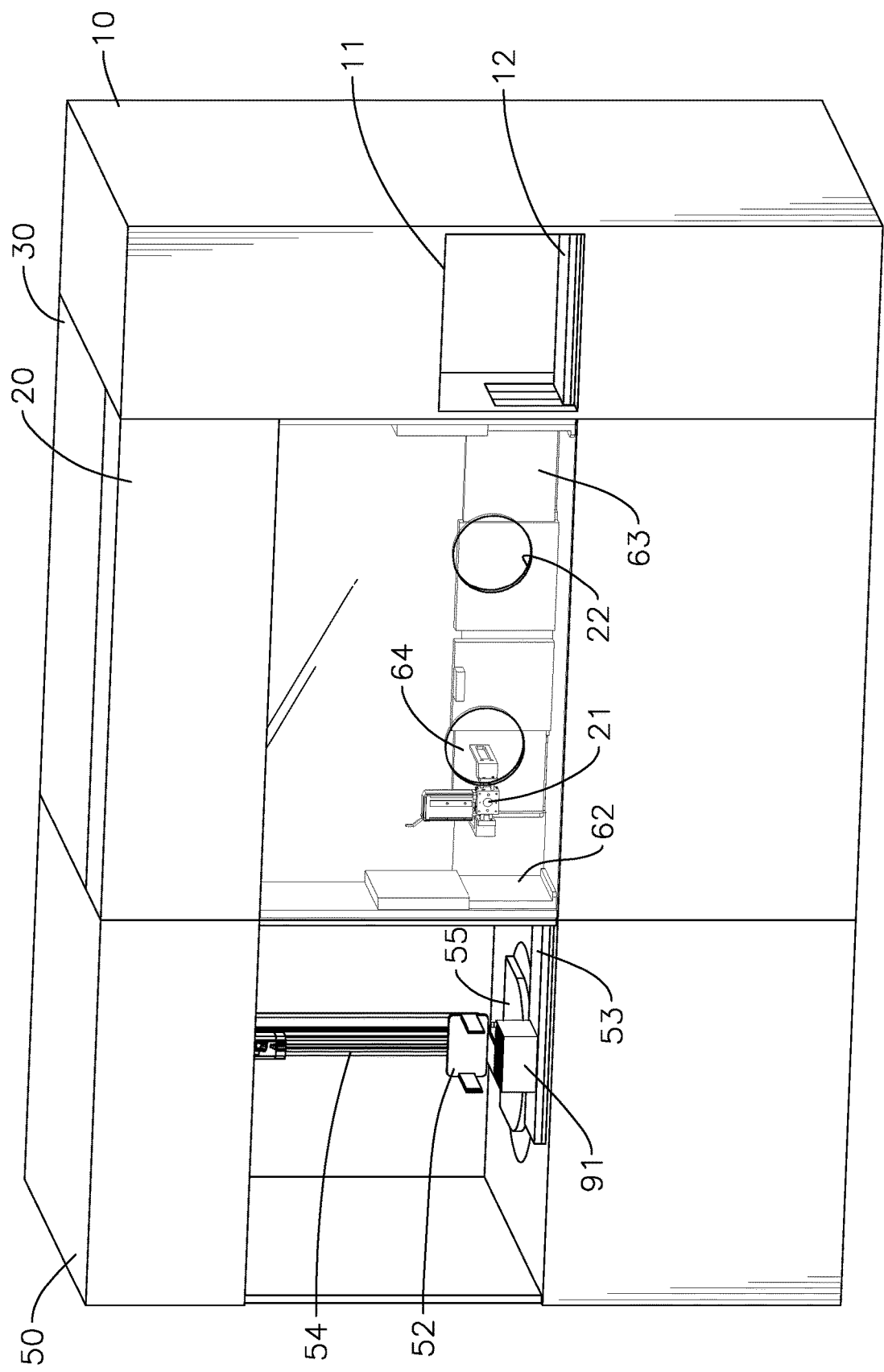
FIG. 14 is an operational view of a freezing container being transferred to the freezing area in accordance with the present invention.

With reference to FIG. 14, the freezer cover 55 is detachably mounted on the freezer, and the freezer cover 55 can automatically open and close, so an interior environment of the freezer may be selectively connected to an exterior environment by the freezer cover 55.

In the present embodiment, the feeding cart 12 and the freezing cart 53 may help automate the whole process, but it is not limited thereto. In another embodiment, in which there is no feeding cart 12 and no freezing cart 53, the user may manually move the freezing container 91 and the temporary storage bottle 92 into the transferring area 20. After that, the user may move the freezing container 91 and the temporary storage bottle 92 within the whole apparatus by the transferring clamp 21 and the freezing clamp 52.

A cell dispensing and storing method comprises steps as follows.

Step (a): With reference to FIGS. 2 and 6, a freezing container 91, a temporary storage bottle 92, a transferring area 20, a transferring clamp 21, a dispensing area 30, and a freezing area 50 are prepared. A test tube 93 is disposed inside the freezing container 91, and a container cover (not shown in figures) is mounted on the freezing container 91. Sample cells (not shown in figures) are contained in the temporary storage bottle 92. In the present method, only one test tube 93 is disposed inside the freezing container 91, but a number of the test tube 93 is not limited thereto; alternatively, multiple test tubes 93 may be disposed in a freezing container 91.

The transferring clamp 21 is mounted in the transferring area 20. At least one operating opening 22 is formed on the transferring area 20. The user may stretch hands into the transferring area 20 through the at least one operating opening 22. The dispensing area 30 comprises a dispensing base 32, a rotating cylinder 33, a rotating platform 34, a tube rack 35, a dispensing clamp 36, and an injecting assembly 40. A rotating clamp 331 is mounted on the rotating cylinder 33. The injecting assembly 40 comprises an injecting nozzle 41, an injecting pipe 42, a nozzle base 43, and a nozzle rack 44. The nozzle rack 44 is mounted on the nozzle base 43. The injecting nozzle 41 is mounted on the nozzle rack 44. One end of the injecting pipe 42 is connected to the injecting nozzle 41. The freezing area 50 comprises a freezer 51 and a freezing clamp 52.

In a preferred embodiment, the structures of the dispensing area 30, elements in the transferring area 20 and the dispensing area 30, and the freezing area 50 and so on are all identical with those of the aforementioned elements, and thus the details thereof are not repeated. However, the elements used in the present method are not limited to the aforementioned elements.

With reference to FIGS. 2 and 3, in step (a), first the user puts the freezing container 91, the injecting nozzle 41 and the injecting pipe 42 into the transferring area 20 through an entrance gate 61. Specifically, the freezing container 91, the injecting nozzle 41, and the injecting pipe 42 are moved into the transferring area 20 by a feeding cart 12. Besides, the injecting nozzle 41 and one end of the injecting pipe 42 are already mutually connected in step (a), but it is not limited thereto.

Step (b): With reference to FIGS. 3, 4, and 6, the user stretches hands into the transferring area 20 through the two operating openings 22, and removes the freezing container 91 and the connected injecting nozzle 41 and the injecting pipe 42 from the feeding cart 12. After the feeding cart 12 leaves the transferring area 20 through the entrance gate 61, the entrance gate 61 is closed up, so the transferring area 20 is isolated and becomes an enclosed space.

After the entrance gate 61 is closed, the transferring gate 63 and the container gate 64 are both open, so the transferring area 20 and the dispensing area 30 are communicating with each other. Then, the freezing container 91 and the injecting pipe 42 are respectively put into the dispensing area 30 through the container gate 64 and the transferring gate 63.

Specifically, after the transferring gate 63 and the container gate 64 are both open, the dispensing base 32 and a nozzle base 43 respectively move from the dispensing area 30 into the transferring area 20. Meanwhile, the user stretches hands from the operating openings 22 into the transferring area 20, and takes the freezing container 91 to a freezing container scanner 23 that is mounted in the transferring area 20, so the freezing container scanner 23 may scan and record the data of the freezing container 91.

After the scanning, the freezing container 91 is put on the dispensing base 32. On the other hand, the moving of the nozzle base 43 from the dispensing area 30 into the transferring area 20 also brings the nozzle rack 44 that is mounted on the nozzle base 43 into the transferring area 20. Then the user stretches hands into the transferring area 20 through the operating openings 22 to connect the injecting nozzle 41 on the nozzle rack 44.

The transferring clamp 21 then removes the container cover from the freezing container 91, and then the dispensing base 32 and the nozzle base 43 move back into the dispensing area 30. After the freezing container 91 and the injecting pipe 42 are moved into the dispensing area 30, the transferring gate 63 and the container gate 64 are closed up again.

After the transferring gate 63 and the container gate 64 are both closed, the transferring area 20 and the dispensing area 30 are sterilized. Specifically, the user may use a computer to start up a UV-C sterilizer lamp to sterilize the feeding area 10, the transferring area 20 and the dispensing area 30. But the sterilizing means is not limited to the UV-C sterilizer lamp.

After the sterilization, the feeding opening 11 is open again, and the user disposes the sterilized temporary storage bottle 92 onto the feeding cart 12 and closes the feeding opening 11. Then the entrance gate 61 is open, so the feeding cart 12 can move the temporary storage bottle 92 into the transferring area 20. After the temporary storage bottle 92 is put into the transferring area 20 through the operating opening 22, the feeding cart 12 leaves the transferring area 20 through the entrance gate 61, and the entrance gate 61 closes up after the feeding cart 12 leaves the transferring area 20.

After the entrance gate 61 is closed, the transferring gate 63 is open, and the nozzle base 43 of the injecting assembly 40 moves the connected injecting nozzle 41 and the injecting pipe 42 into the transferring area 20 with the nozzle rack 44. The user stretches hands through the operating opening 22 and into the transferring area 20, and connects another end of the injecting pipe 42 with the temporary storage bottle 92, so the injecting pipe 42 is capable of extracting sample cells in the temporary storage bottle 92. After the injecting pipe 42 is connected to the temporary storage bottle 92, the nozzle base 43 moves the injecting nozzle 41, the injecting pipe 42 and the temporary storage bottle 92 back into the dispensing area 30 through the transferring gate 63. Then the transferring gate 63 is closed again, so the dispensing area 30 that has the freezing container 91 and the temporary storage bottle 92 becomes an enclosed space.

The method for moving the injecting pipe 42 and the temporary storage bottle 92 is not limited to the aforementioned. Alternatively the injecting pipe 42 and the temporary storage bottle 92 can be moved between the transferring area 20 and the dispensing area 30.

Besides, in step (b), before the freezing container 91 is moved to the dispensing base 32 by the transferring clamp 21, the user may pick up the freezing container 91 through the operating opening 22 and move it to the freezing container scanner 23 in the transferring area 20 to record data from said freezing container 91.

Step (c): With reference to FIGS. 7, 8, and 9, the dispensing clamp 36 moves the test tube 93 from the freezing container 91 to the tube rack 35 of the rotating platform 34, and then the rotating platform 34 moves the tube rack 35 around to a position below the rotating clamp 331 of the rotating cylinder 33. Specifically, in step (c), a rotating angle of the rotating platform is, but not limited to, 90 degrees counterclockwise. In another embodiment, the rotating direction can be clockwise. After the rotation of the rotating platform 34, the tube rack 35 is moved to the position below the rotating clamp 331. Then the rotating clamp 331 moves downwardly and removes a tube cover 94 from the test tube 93. In the preferred embodiment, the tube cover 94 is screwed on the test tube 93. Therefore to remove the tube cover 94, the rotating clamp 331 has to hold the tube cover 94, rotate the tube cover 94, and finally lift the tube cover 94 up from the test tube 93, and then the rotating clamp 331 moves upwardly with the tube cover 94, so the test tube 93 is left on the tube rack 35 without the tube cover 94.

In other embodiments, the moving process of the rotating clamp 331 is not limited to the aforementioned, and can be adjusted with different connecting methods between the test tube 93 and the tube cover 94.

Step (d): With reference to FIGS. 9, 10, and 11, the rotating platform 34 moves the tube rack 35 to a site adjacent to the injecting assembly 40. Specifically, in the present embodiment, the rotating angle of the rotating platform 34 is 90 degrees counterclockwise, same as in the previous step, so the tube rack 35 is moved to a site adjacent to the injecting nozzle 41, and then the injecting nozzle 41 extracts sample cells from the temporary storage bottle 92 and dispenses them into the test tube 93, which is uncovered, through the injecting pipe 42.

Figure 12:
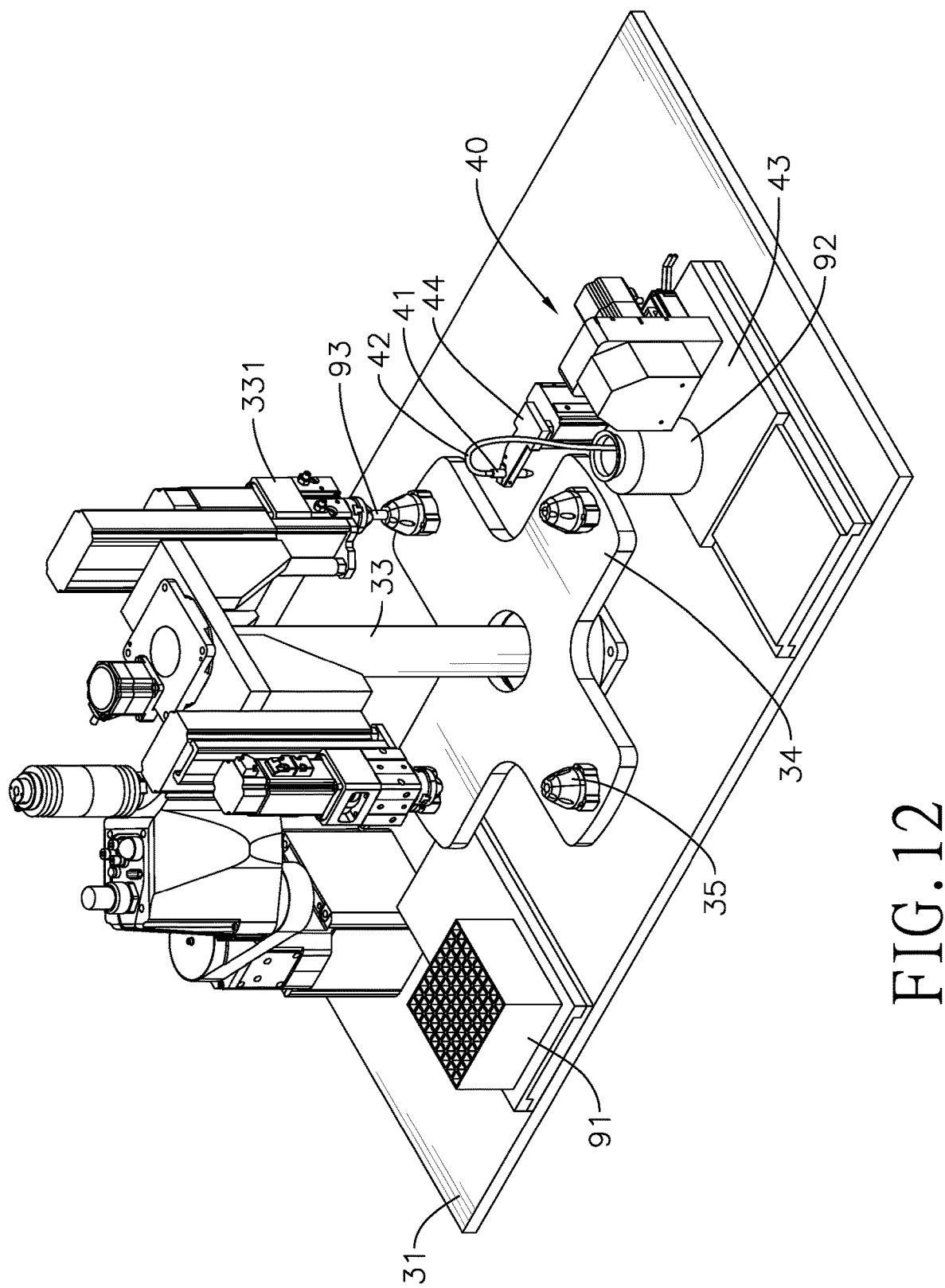

Step (e): With reference to FIGS. 11 and 12, the rotating cylinder 33 and the rotating clamp 331 move together. The rotating platform 34 moves the test tube 93 to the position below the rotating clamp 331. Specifically, in the present step, the rotating cylinder 33 and the rotating clamp 331 rotate along the rotating direction for 180 degrees, and the rotating platform 34 rotates along the rotating direction for 90 degrees. When the test tube 93 is moved to the position below the rotating clamp 331, the rotating clamp 331 moves downwardly and puts the tube cover 94 back onto the test tube 93.

Figure 13:
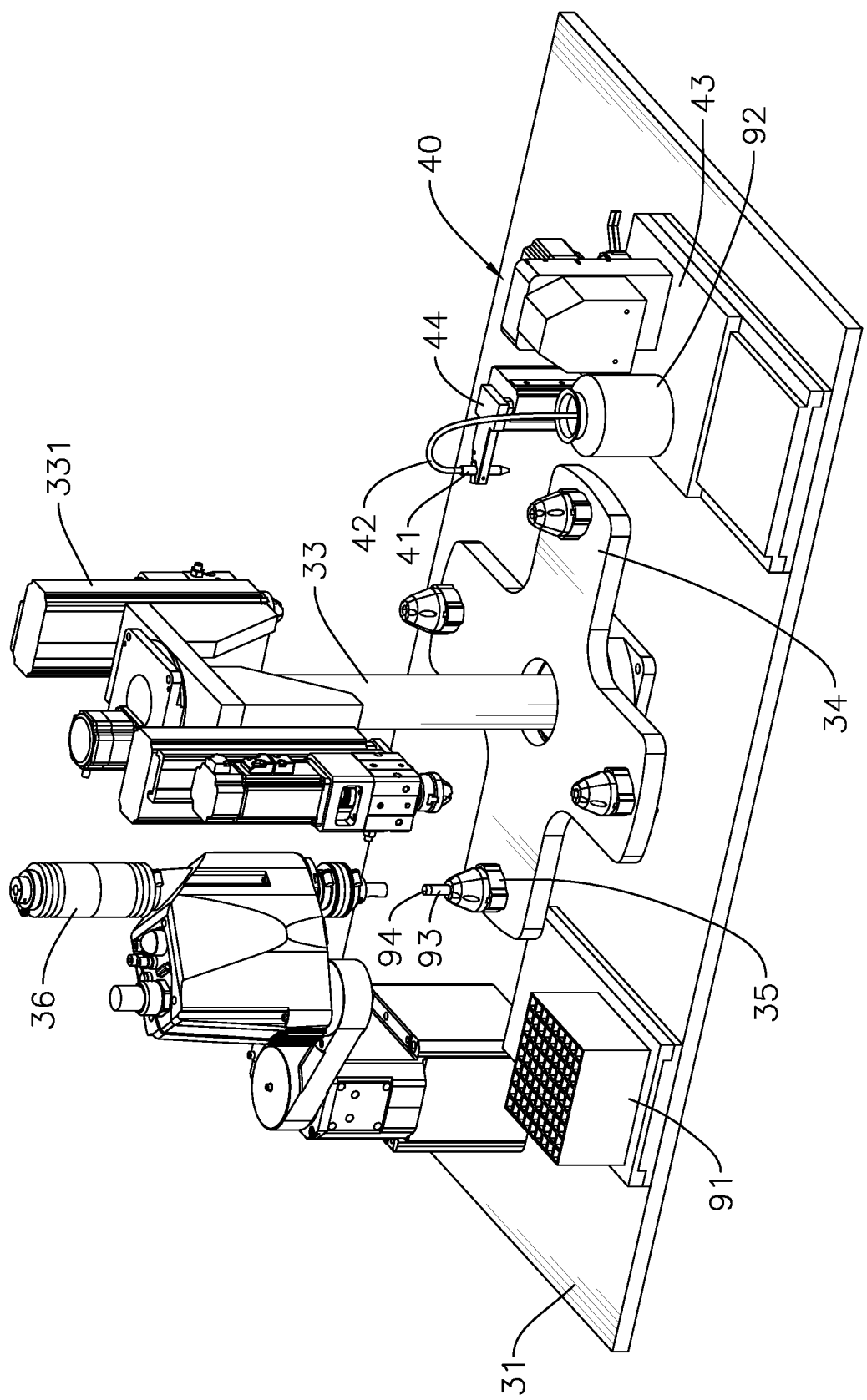

Step (f): With reference to FIGS. 12 and 13, the rotating platform 34 moves the tube rack 35 to a site adjacent to the dispensing clamp 36. Specifically, in step (f), the rotating platform 34 moves the tube rack 35 to the site adjacent to the dispensing clamp 36 by rotating along the rotating direction for 90 degrees. Then, the dispensing clamp 36 moves the test tube 93 from the tube rack 35 into the freezing container 91, finishing the dispensing process. After the dispensing process, the container gate 64 is open, the dispensing base 32 moves the freezing container 91 into the transferring area 20, and the transferring clamp 21 restores the container cover back onto the freezing container 91. Then the transferring clamp 21 lifts up the freezing container 91 from the dispensing base 32 and puts it in the transferring area 20, and the dispensing base 32 moves back to the dispensing area 30. Finally, the container gate 64 is closed up.

Step (g): With reference to FIGS. 3 and 14, an exit gate 62 is open, so the freezing area 50 communicates with the transferring area 20. A freezing cart 53 moves from the freezing area 50 through the exit gate 62 into the transferring area 20, the transferring clamp 21 moves the freezing container 91 from the transferring area 20 onto the freezing cart 53, and the freezing cart 53 moves back to the freezing area 50 with the freezing container 91. Then the exit gate 62 is closed up. The freezing cart 53 moves the freezing container 91 to a site adjacent to the freezer 51, a freezer cover 55 of the freezer 51 opens, and then a freezing clamp 52 holds the freezing container 91 and moves the freezing container 91 into the freezer 51. After the freezing clamp 52 leaves the freezer 51, the storage process is completed. In step (g), the exit gate 62 is closed up after the freezing container 91 is moved into the freezing area 50, so the freezing area 50 becomes an enclosed space.

By the aforementioned steps, the present invention automatically dispenses and stores sample cells. The present invention can largely lower the required human labor for dispensing sample cells, and also can ensure the whole dispensing process is processed in an enclosed space without any outer interference, therefore the present invention can effectively avoid the risk of the sample cells being infected by germs or other contaminations and losing the characteristic for inspection.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A cell dispensing and storing apparatus comprising:
   a feeding area comprising
      a feeding opening formed on a wall of the feeding area and communicating with an exterior environment;
   a transferring area selectively communicating with the feeding area and comprising
      a transferring clamp movably disposed in the transferring area; and
      at least one operating opening formed on a wall of the transferring area;
   a dispensing area selectively communicating with the transferring area and comprising
      a dispensing platform mounted in the dispensing area;
      a dispensing base movably mounted on the dispensing platform and being capable of moving from the dispensing area into the transferring area;
      a rotating cylinder rotatably mounted on the dispensing platform;
      at least one rotating clamp mounted on the rotating cylinder and being capable of moving up and down relative to the rotating cylinder; each of the at least one rotating clamp having
         a mounting segment mounted on the rotating cylinder and being capable of moving up and down relative to the rotating cylinder; and
         a clamping segment mounted on the mounting segment and being capable of rotating relative to the mounting segment;
      a rotating platform rotatably mounted on the dispensing platform and being capable of rotating relative to the rotating cylinder;
      multiple tube racks mounted on the rotating platform, surrounding the rotating cylinder, and being capable of rotating relative to the rotating cylinder through a rotation of the rotating platform, wherein the at least one rotating clamp is capable of moving to a top of each one of the tube racks;
      a dispensing clamp mounted on the dispensing platform and being capable of moving to a top of the dispensing base and to the top of one of the tube racks; and
      an injecting assembly mounted on the dispensing platform and comprising
         a nozzle rack mounted on the dispensing platform;
         an injecting nozzle mounted on the nozzle rack and disposed on the top of one of the tube racks; and
         an injecting pipe, one end of the injecting pipe connected to the injecting nozzle; and
   a freezing area selectively communicating with the transferring area and comprising
      a freezer mounted in the freezing area; and
      a freezing clamp movably mounted in the freezing area and being capable of moving into the freezer.

2. The cell dispensing and storing apparatus as claimed in claim 1 further comprising:
   a feeding cart disposed in the feeding area and being capable of moving from the feeding area into the transferring area; and
   a freezing cart disposed in the freezing area and being capable of moving from the freezing area into the transferring area.

3. The cell dispensing and storing apparatus as claimed in claim 1 further comprising a gate assembly; the gate assembly comprising:
   an entrance gate mounted between the feeding area and the transferring area, wherein the entrance gate selectively closes a first opening between the feeding area and the transferring area;
   an exit gate mounted between the transferring area and the freezing area, wherein the exit gate selectively closes a second opening between the transferring area and the freezing area;
   a transferring gate mounted between the transferring area and the dispensing area and being adjacent to the feeding area, wherein the transferring gate selectively closes a third opening between the transferring area and the dispensing area; and
   a container gate mounted between the transferring area and the dispensing area and being adjacent to the freezing area, wherein the container gate selectively closes a fourth opening between the transferring area and the dispensing area.

4. The cell dispensing and storing apparatus as claimed in claim 2 further comprising a gate assembly, the gate assembly comprising:
   an entrance gate mounted between the feeding area and the transferring area, wherein the entrance gate selectively closes a first opening between the feeding area and the transferring area;
   an exit gate mounted between the transferring area and the freezing area, wherein the exit gate selectively closes a second opening between the transferring area and the freezing area;
   a transferring gate mounted between the transferring area and the dispensing area and being adjacent to the feeding area, wherein the transferring gate selectively closes a third opening between the transferring area and the dispensing area; and
   a container gate mounted between the transferring area and the dispensing area and being adjacent to the freezing area, wherein the container gate selectively closes a fourth opening between the transferring area and the dispensing area.

5. The cell dispensing and storing apparatus as claimed in claim 1, wherein the transferring area further comprises a freezing container scanner, and the freezing container scanner is mounted adjacent to the at least one operating opening.

6. The cell dispensing and storing apparatus as claimed in claim 4, wherein the transferring area further comprises a freezing container scanner, and the freezing container scanner is mounted adjacent to the at least one operating opening.

\* \* \* \* \*